United States Patent [19]

Buzzanca et al.

[11] Patent Number: 4,564,436
[45] Date of Patent: Jan. 14, 1986

[54] APPARATUS FOR MEASURING THE DEGREE OF SENSITIZATION OF METAL ARTICLES

[75] Inventors: Giovanni Buzzanca, Bergamo; Camillo Ronchetti, Milan; Franco Uberti, Milan; Renato Anzani, Milan, all of Italy

[73] Assignee: CISE-Centro Informazioni Studi Esperienze S.p.A., Milan, Italy

[21] Appl. No.: 739,015

[22] Filed: May 29, 1985

[30] Foreign Application Priority Data

Jun. 1, 1984 [IT] Italy .................................. 21225 A/84

[51] Int. Cl.⁴ ............................................. G01N 27/02
[52] U.S. Cl. ..................................... 204/400; 204/404; 204/412; 324/71.1
[58] Field of Search ............... 204/400, 404, 412, 1 C, 204/1 T; 324/71.1

[56] References Cited

U.S. PATENT DOCUMENTS

| | | | |
|---|---|---|---|
| 4,006,063 | 2/1977 | Ensanian | 204/1 T |
| 4,133,722 | 1/1979 | Ensanian | 204/1 T |
| 4,179,349 | 12/1979 | Park | 204/400 X |
| 4,515,643 | 5/1985 | Knaster | 148/6.15 Z |

Primary Examiner—G. L. Kaplan
Attorney, Agent, or Firm—Stevens, Davis, Miller & Mosher

[57] ABSTRACT

An apparatus for measuring the degree of sensitization of metal articles comprises an electrochemical cell in which the potential of a test-piece of the article with respect to a reference electrode is made to vary linearly with time by feeding currents of suitable intensity from the passivation field to the activation field by means of the counter-electrode; a pair of electrodes moves along the test-piece surface with the respective electrode ends kept equidistant and disposed along an axis substantially perpendicular to the test-piece surface, one of them being in contact with said surface; by measuring the potential difference of this pair of electrodes as a function of their position, the local degree of sensitization of the test-piece is obtained.

4 Claims, 6 Drawing Figures

APPARATUS FOR MEASURING THE DEGREE OF SENSITIZATION OF METAL ARTICLES

This invention relates to an apparatus for measuring the degree of sensitisation of metal articles.

The sensitisation of a metal article denotes its chemical alteration at the intergranular level due to particular treatment which it has undergone, for example heat treatment. The higher the sensitisation of the metal article, the greater its susceptibility to corrosion by external chemical agents.

An apparatus has been proposed for measuring said degree of sensitisation which uses electrochemical principles for its operation. The apparatus comprises an electrochemical cell, in the bath of which there is immersed a test-piece of the metal article which is to have its degree of sensitisation measured.

For this measurement, the apparatus comprises a working electrode constituted by the test-piece itself, a counter-electrode and a reference electrode, these also being immersed in the bath, the latter in proximity to the test-piece. The potential of the test-piece with respect to the reference electrode is varied linearly with time by feeding currents of suitable intensity from the passivation field to the activation field by way of the counter-electrode. The function defined by current density (fed by the counter-electrode)v. electrochemical potential (between the test-piece and reference electrode) is recorded, this being known as the potentiodynamic reactivation curve. This curve comprises a peak. The degree of sensitisation $P_a$ is expressed as the reactivation charge density Q, represented by the area of the peak of the potentiodynamic reactivation curve, standardised for the material grain size. The relative formula is as follows:

$$P_a = Q/GBA$$

where GBA is the specific grain boundary area of the metal article under examination.

This apparatus is practical and effective when the metal article has uniform sensitisation.

However, problems arise when the metal article does not have uniform sensitisation, for example when the metal article comprises zones welded together.

In this respect, the degree of sensitisation in the weld seam zone of the metal article, known as the heat-affected zone, varies from point to point.

In such a case, the described apparatus requires the measurement to be made point by point, because a single overall measurement of the degree of sensitisation of the heat-affected zone would give a meaningless average value.

It is therefore necessary to isolate small portions which make up the heat-affected zone, and measure the degree of sensitisation on each one.

This is obviously a long and laborious operation, as an entire series of measurements has to be made. In addition, it only gives a discrete and non-continuous view of the distribution of the degree of sensitisation along the heat-affected zone, as a measurement over infinitessimal portions of the article can obviously not be made. A more complicated apparatus has been proposed to obviate these drawbacks (B. Vyas, H. S. Isaacs—Detecting susceptibility to intergranular corrosion of stainless steel weld heat-affected zones, R. F. Steigerwald, editor ASTM-STP 656).

This apparatus comprises the components described for the preceding apparatus, plus a second fixed reference electrode immersed in the electrochemical bath in proximity to a zone of the metal article which has not been heat-affected, and a reference electrode mobile in the electrochemical bath along a surface adjacent and parallel to the surface of the metal article at the heat-affected zone.

In making the measurement, the potentiodynamic reactivation curve is recorded in the manner described for the preceding apparatus, and the mobile reference electrode is moved along a line contained within said surface adjacent and parallel to the surface of the metal article at the heat-affected zone. The mobile reference electrode is moved or made to scan during the time interval in which the potentiodynamic curve is at the highest current density values. A curve is then drawn of the potential difference between the mobile reference electrode and the second fixed electrode as a function of the position of the mobile reference electrode along said line.

This potential difference curve gives a pattern of the sensitisation of the metal article along said scanning line. This pattern is however only qualitiative in that it does not enable numerical values of the degree of sensitisation to be obtained.

It is however important for experts of the art to obtain a numerical value for the degree of sensitisation of metal articles which are not uniformly sensitised, in order to exactly know their susceptibility to corrosion both in absolute terms for each article and for comparing one with another.

The object of the present invention is to propose an apparatus which enables the degree of sensitisation of non-uniformly sensitised metal articles to be quantitatively measured.

This object is attained by an apparatus for measuring the degree of sensitisation of metal articles, comprising a cell containing an electrochemical solution which wets at least a portion of the metal article under measurement, a first electrode unit constituted by the test-piece itself, a second counter-electrode unit immersed in the electrochemical solution, a third reference electrode unit immersed in the electrochemical solution in proximity to said portion under measurement, means for feeding an electric current through said first electrode unit and said second counter-electrode unit, and means for controlling said feed means in such a manner as to impose a linear variation in the potential difference between said first electrode unit and said third reference electrode unit, characterised by comprising a fourth and a fifth electrode unit which are secured in such a manner as to maintain a constant distance apart and are supported by a support and drive assembly which drives them along a surface of the portion of the metal article, said fourth and fifth electrode units having respective sensing ends disposed along an axis which remains substantially perpendicular to said surface during the driving of said fourth and fifth electrode units along it, one of said sensing ends resting on said surface, means also being provided for measuring the potential difference between said fourth and fifth electrode units as a function of their position along said surface.

The characteristics and operation of the apparatus according to the invention will be apparent from the description of a non-limiting embodiment thereof given hereinafter and illustrated on the accompanying drawings in which.

Figure 1:
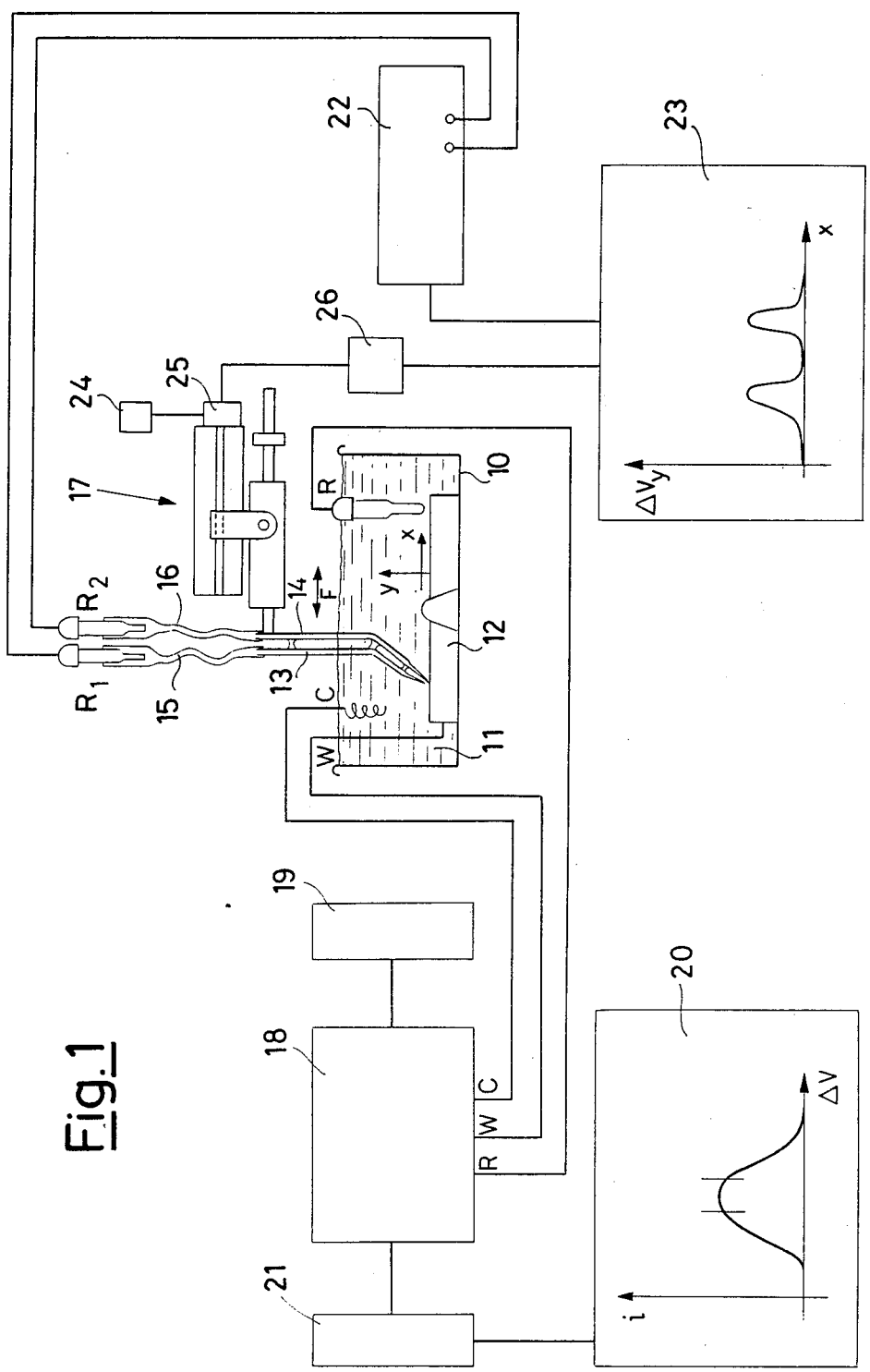
FIG. 1 is an overall diagrammatic view of the apparatus according to the invention.

The apparatus of FIG. 1 comprises an electrochemical-mechanical part and an electronic part.

The electrochemical-mechanical part comprises a cell 10 containing an electrochemical solution 11 which completely wets the test-piece 12 of the metal article (for example of stainles steel) of which the degree of sensitisation is to be measured. A counter-electrode C constituted by a platinum wire and a reference electrode R are immersed in the solution 11. In the solution 11 there are also immersed two capillaries 13 and 14 which are rigidly connected together. The two capillaries 13 and 14 extend into two respective flexible tubes 15 and 16. An electrode $R_1$ is inserted into the tube 15 and an electrode $R_2$ is insered into the tube 16. The two capillaries 13 and 14 and the two respective tubes 15 and 16 are filled with an electrochemical solution identical to the solution 11. The two capillaries 13 and 14 are mounted on a support and drive assembly 17 which is described in detail hereinafter. The support and drive assembly 17 moves the two capillaries 13 and 14 along an axis x of the surface of the test-piece 12, as indicated by the double arrow F. It should be noted that, for reasons explained hereinafter, the mutual positioning of the two capillaries 13 and 14 and their positioning on the support and drive assembly 17, and also the positioning of the support and drive assembly itself, are such that the ends of the capillaries lie substantially along an axis y perpendicular to the surface of the test-piece 12 over their entire path of travel along the x axis, and that one of the two capillaries, namely the lower one (which in the example is the capillary 14), is always in contact with said surface.

The electronic part comprises a potentiostat 18 connected to the test-piece 12 which itself constitutes an electrode, namely the working electrode and indicated by W, and is also connected to the counter-electrode C and to the reference electrode R. A function generator 19 is connected to the potentiostat 18. In the potentiostat there is incorporated an ammeter which feeds the measured signal to a recorder-display unit 20 by way of an interface 21. The two electrodes $R_1$ and $R_2$ are connected to an electrometer 22, which feeds the measured signal to a recorder-display unit 23. There are also provided a switch 24 which controls a motor 25 of the drive assembly, and a position transducer 26 which is connected to the motor 25 and in practice feeds to the recorder-display unit 23 the signal corresponding to the position of the pair of electrodes 13 and 14 along the x axis.

As stated, FIGS. 2 to 5 show details of the electrochemical-mechanical part of the apparatus of FIG. 1. In particular, the apparatus is applied to a pipe 27 in order to measure the degree of sensitisation of a portion thereof corresponding to the test-piece 12 of FIG. 1, in the position of a weld seam 28, ie in a heat-affected zone.

Figure 2:
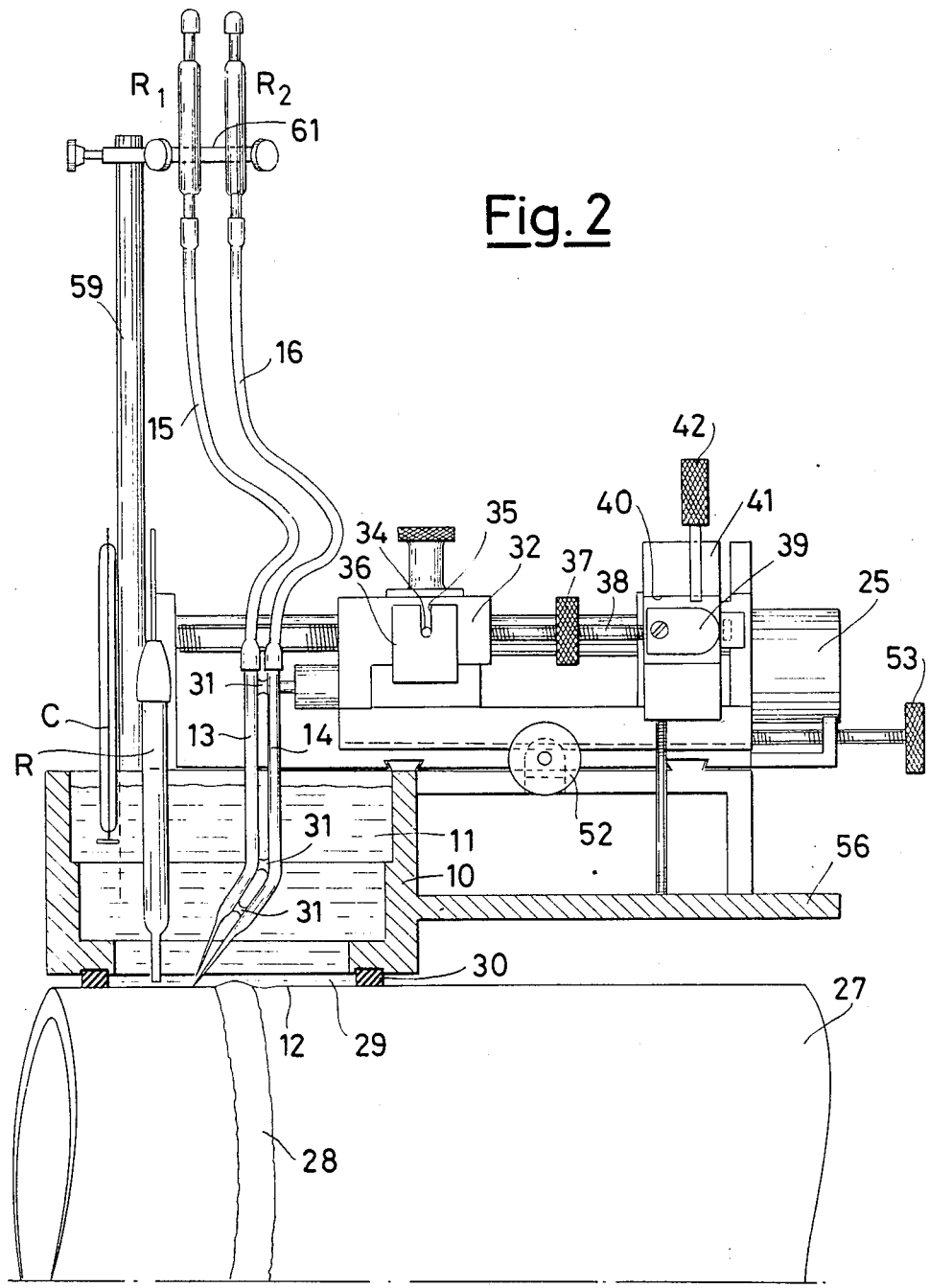
FIG. 2 is a detailed elevational view of the electrochemical-mechanical part of the apparatus of FIG. 1.
Figure 3:
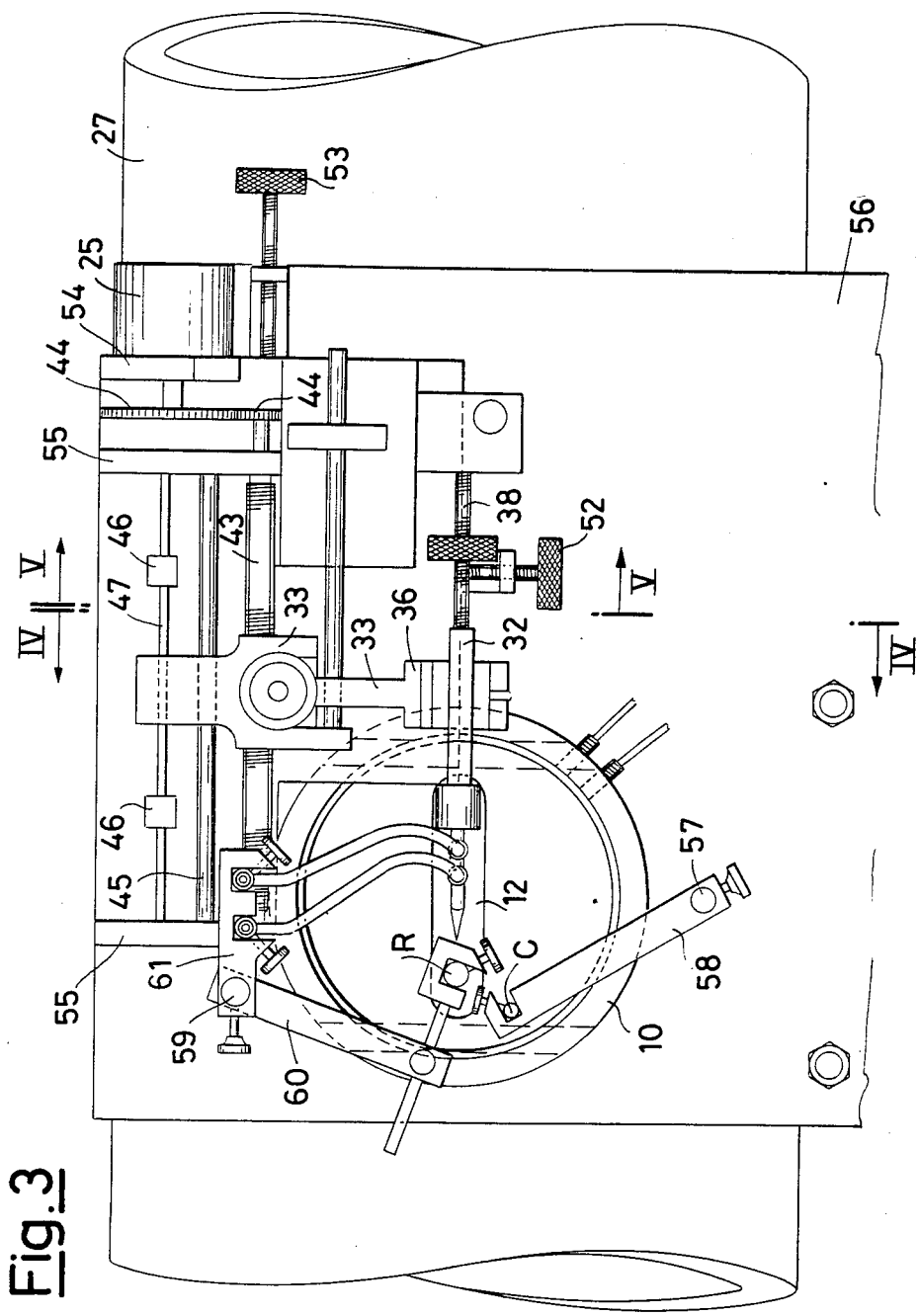
FIG. 3 is a plan view of the electrochemical-mechanical part of the apparatus shown in FIG. 2.
Figure 4:
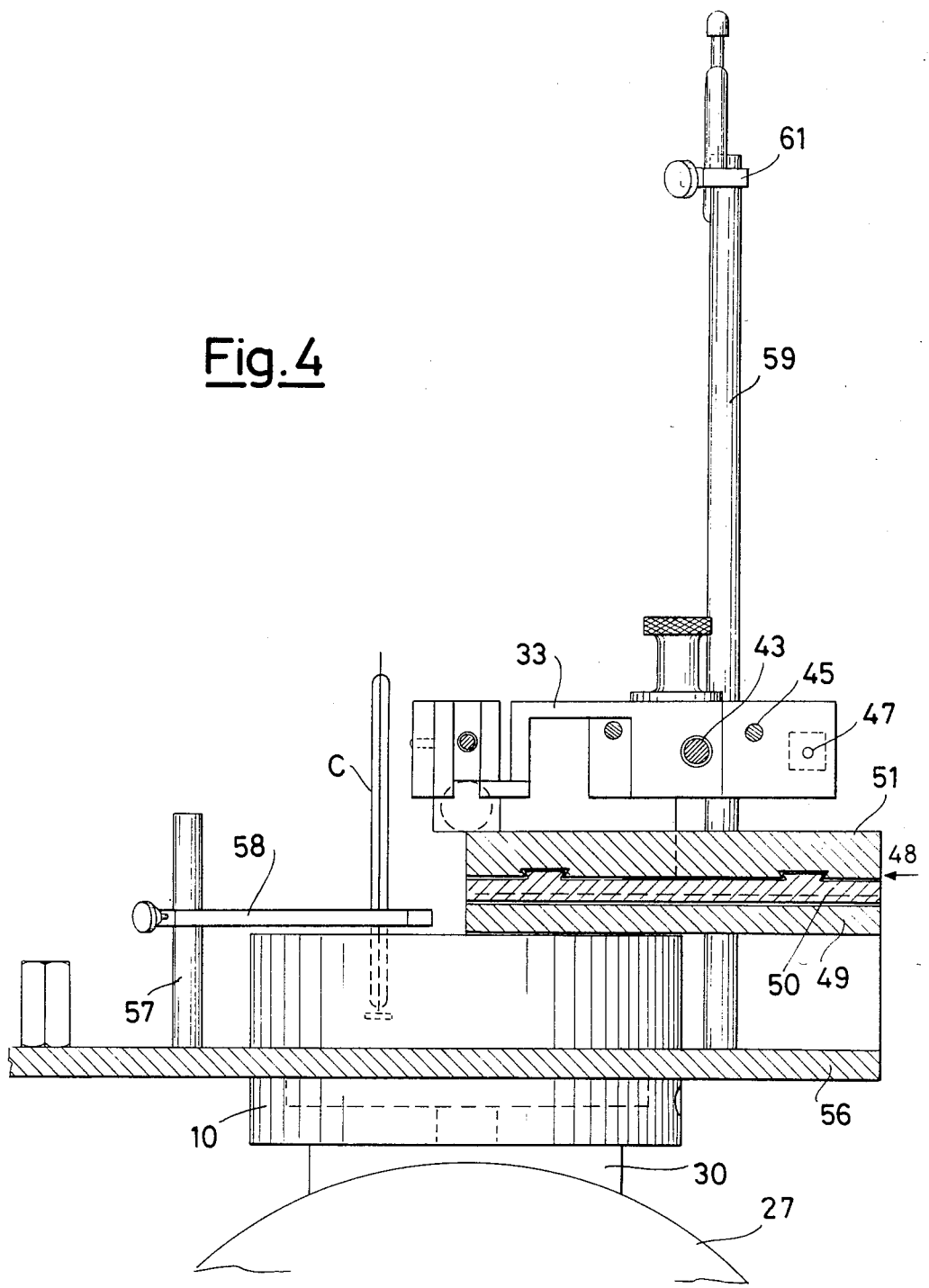
FIG. 4 is a section on the line IV—IV of FIG. 3.
Figure 5:
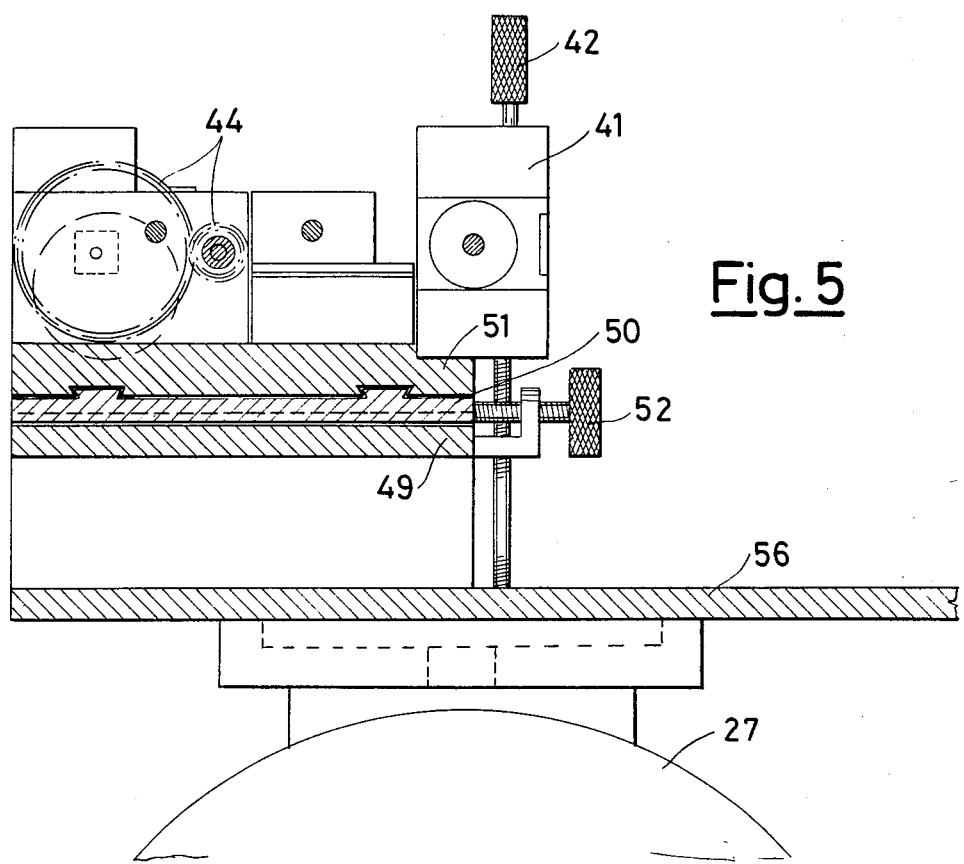
FIG. 5 is a section on the line V—V of FIG. 3.

For this purpose, the cell 10 comprises an aperture 29 in its base and rests on gaskets 30 about said aperture 29, so that the electrochemical solution 11 wets the portion 12 (test-piece) but does not leak from the cell 10, as shown in FIG. 2.

The two capillaries 13 and 14 are fixed rigidly together by webs 31. The pair of capillaries 13 and 14 is supported by one end of an arm 32 mounted in such a manner as to rock about a second transverse are 33. This is attained by a connection made by a through pin 34 in the arm 32, which engages in two corresponding opposing cavities 35 in a terminal U-shaped portion 36 of the transverse arm 33, in which the arm 32 is inserted and rocks. The arm 32 has a threaded portion 37 on which a wheel 38 is screwed to act as an adjustable counterweight for the pair of capillaries 13 and 14. The free end of the arm 32 comprises a lug 39 which is received in a seat 40 of a block 41 in which the lug 39 has a certain space for oscillation. A screw 42 is screwed into the block 41 to penetrate into the seat 40 in order to limit the upward path of travel of the lug 39, as shown in FIG. 2.

The arm 33 is moved along a direction parallel to the axis x of the motor 25 by a worm 43 which is screwed through the arm 33 and by gear wheels 44 which link the motor 25 to the worm 43. The arm 33 is guided in this movement by a rod 45 parallel to the worm 43. In order to delimit the path of travel of the arm 33, there are provided two opposing limit switches 46 mounted on a further rod 47 along which the arm 33 slides, they being operated by the arm 33 which slides between them, to interrupt the electricity supply to the motor 25.

The entire described support and drive assembly 17 for the pair of capillaries 13 and 14 is supported by a multiple slide 48. The slide 48, of known type, comprises a fixed base 49 on which a lower plate 50 can slide along one direction and be locked in position, on the lower plate there being able to slide an upper plate 51 along a direction perpendicular to the preceding and be locked in position. The movement of the lower plate 50 is regulated by a screw 52, and the movement of the upper plate 51 is regulated by a screw 53. On the upper plate 51 there are fixed a shoulder 54 which supports the motor 25 and a pair of shoulders 55 which support the worm 43, the guide rod 45 and the rod 47.

The base 49 of the slide 48 is mounted rigidly on a baseplate 56 fixed to the pipe 27.

On the baseplate 56 there are also rigidly mounted a vertical rod 57 to which there is fixed an arm 58 carrying the counter-electrode C, and a vertical rod 59 to which there is fixed an arm 60 carrying the reference electrode R, and to the top end of which there is fixed an arm 61 carrying the electrodes $R_1$ and $R_2$. The operation of the apparatus is as follows.

The potential of the test piece 12 (working electrode W) with respect to the reference electrode R is made to vary linearly with time by feeding currents of suitable intensity through the counter-electrode C from the passivation field to the activation field, by means of the potentiostat 18 and the function generator 19, using a known method analogous to that described in the introduction relative to the first apparatus. The current density i fed by the counter-electrode C is measured by the incorporated ammeter and is processed in the potentiostat as a function of the electrochemical potential $\Delta V$ between the test-piece and reference electrode, to obtain the potentiodynamic reactivation curve which is recorded and displayed at 20 by way of the interface 21.

This curve is shown in FIG. 1 in the recorder-display block 20.

During the time interval in which the potentiodynamic curve is at its highest current density values (between the two portions of the graph in 20) the pair of capillaries 13 and 14 are driven from left to right along the x axis through the heat-affected zone transversely to the weld seam 28 of the pipe 27. The instant of commencement and termination of the movement can be determined visually by the operator by observing the time pattern of the potentiodynamic reactivation curve on the recorder-display unit 20, and operating the motor 25 by the switch 24 when the curve is turning towards its peak value, then stopping the motor 25 as the curve leaves its maximum values. This can also be done automatically by means of a processing and control device which calculates the derivative of the potentiodynamic curve in question and operates the motor 25 between a positive and a negative derivative value about zero derivative. With regard to the movement of the pair of capillaries 13 and 14, the counterweight 37 must be in a position along the rocker arm 38 such that the capillary 14 is always in contact with the surface of the test-piece 12 by the action of their actual weight during the movement. The potential difference $\Delta V_y$ between the electrode $R_1$ and the electrode $R_2$, corresponding to the potential difference between the ends of the capillaries in the solution 11, is measured by the electrometer 22 during the entire movement of the two capillaries 13 and 14 along the x axis. The transducer 26 converts the signal indicating the angular position of the motor 25 into a signal indicating the position of the pair of capillaries 13 and 14 along the x axis. The signal $\Delta V_y$ measured by the electrometer 22 and the position signal of the transducer 26 are fed to the recorder-display unit 23 to enable this to display the curve $\Delta V_y$ as a function of x (shown in the block 23), i.e. the potential difference between the ends of the capillaries 13 and 14 as a function of their position along the x axis.

From the value $\Delta V_y$ it is possible to obtain the value point-by-point or local value of the degree of sensitisation $P_a$, equal to Q/GBA, of the test piece 12 along the x axis, i.e. the object as stated in the introduction, in the following manner.

Figure 6:
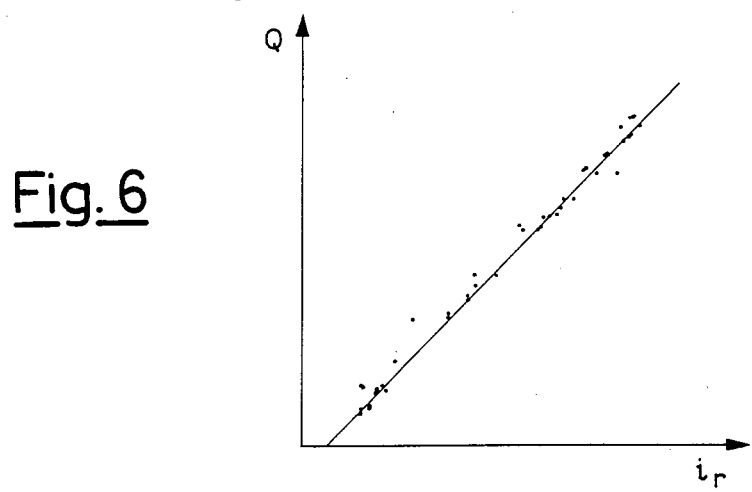
FIG. 6 is a graph which is designed to enable the degree of sensitisation to be calculated by the apparatus of FIG. 1.

The distribution of the potential difference $\Delta V_y$ measured between the electrodes 13 and 14 during scanning along the x axis is related to the distribution of the local corrosion current density $i_r$ at the peak values of the potentiodynamic reactivation curve by the relationship $$i_r = \sigma(\Delta V_y/\Delta y),$$

where $\sigma$ is the conductivity of the solution 11 at the test temperature and $\Delta y$ is the distance between the two ends of the capillaries 13 and 14. As $\sigma$, $\Delta V_y$ and $\Delta y$ are known, the value $i_r$ can be calculated. In order to obtain the distribution of the peak charge density Q from the distribution of current density $i_r$, an experimental correlation is used which is shown in FIG. 6. This is obtained experimentally by measuring the value Q for each value of $i_r$ for a series of test-pieces of the same metal as the test-piece 12, but each being uniformly sensitised with a different sensitivity. The value $P_a$ is obtained from Q using the formula given in the introduction, after calculating the local values of the grain boundary area GBA.

The described quantitative measurement is possible because of the fact that the local corrosion current density $i_r$ can be calculated, this being in a direction perpendicular to the surface of the test-piece 12 scanned by the two capillaries 13 and 14. This is possible because of the special arrangement of the ends of the two capillaries 13 and 14, which are disposed along said perpendicular direction. In the second known apparatus described in the introduction this is not possible because it only measures the current density in the electrochemical solution along a direction parallel to the test-piece surface.

It is preferable, but not necessary, to make the capillaries 13 and 14 scan along the x axis when the potentiodynamic reactivation curve is at its peak values, in that it is precisely within the corresponding time interval that the degree of sensitisation of the test-piece 12 along the x axis is conventionally measured. Starting from the moment in which the potentiostat begins to operate, it is also possible to carry out a series of scannings at different speeds with the capillaries 13 and 14 independently of the potentiodynamic reactivation curve, until the curve $\Delta V_y$ as a function of x is obtained which corresponds to the conventional measurement of the degree of sensitisation, even though this is more laborious. The multiple slide 48 enables the pair of capillaries 13 and 14 to be initially positioned, by adjusting the two adjustment screws 52 and 53.

Obviously, more complicated support and drive assemblies can be provided, able to move the two capillaries 13 and 14 not only along rectilinear trajectories but also along curved trajectories over the test-piece surface.

We claim:

1. An apparatus for measuring the degree of sensitisation of metal articles, comprising a cell containing an electrochemical solution which wets at least a portion of the metal article under measurement, an electrical contact adapted to be connected to a test-piece acting as a first electrode, a second counter-electrode unit immersed in the electro-chemical solution, a third reference electrode unit immersed in the electrochemical solution in proximity to said portion under measurement, means for feeding an electric current through said first electrode unit and said second counter-electrode unit, and means for controlling said feed means in such a manner as to impose a linear variation in the potential difference between said first electrode unit and said third reference electrode unit, characterised by comprising a fourth and a fifth electrode unit which are secured in such a manner as to maintain a constant distance apart and are supported by a support and drive assembly which drives them along a surface of the portion of the metal article, said fourth and fifth electrode units having respective sensing ends disposed along an axis which remains substantially perpendicular to said surface during the driving of said fourth and fifth electrode units along it, one of said sensing ends resting on said surface, means also being provided for measuring the potential difference between said fourth and fifth electrode units as a function of their position along said surface.

2. An apparatus as claimed in claim 1, characterised by comprising means for operating said support and drive assembly during a time interval in which the curve of the electric current density through said first electrode unit and said second counter-electrode unit as a function of said potential difference between said first electrode unit and said third reference electrode unit is at its highest values.

3. An apparatus as claimed in claim 1, characterised in that said fourth and fifth electrode units are rigidly joined together and are fixed to one end of an arm of said support and drive assembly which is mounted in said assembly in such a manner as to rock about a pin and is provided at its other end with an adjustable counterweight.

4. An apparatus as claimed in claim 1, characterised in that said fourth and fifth electrode units comprise a pair of capillaries immersed in the electrochemical solution, one end of each capillary being connected to a respective electrode, the other end constituting said sensing end.

* * * * *